United States Patent
Julien et al.

(10) Patent No.: US 11,426,575 B2
(45) Date of Patent: Aug. 30, 2022

(54) CONNECTION METHOD FOR CONNECTING AN ISOLATED MICRO-CONDUCTOR

(71) Applicant: Sorin CRM SAS, Clamart (FR)

(72) Inventors: Etienne Julien, Paris (FR); Nicolas Shan, Antony (FR); Daniel Kroiss, Saint Ismier (FR)

(73) Assignee: Sorin CRM SAS, Clamart (FR)

( * ) Notice: Subject to any disclaimer, the term of this patent is extended or adjusted under 35 U.S.C. 154(b) by 425 days.

(21) Appl. No.: 16/460,917

(22) Filed: Jul. 2, 2019

(65) Prior Publication Data
US 2020/0009370 A1 Jan. 9, 2020

(30) Foreign Application Priority Data
Jul. 6, 2018 (FR) ........................................ 1856248

(51) Int. Cl.
*A61N 1/05* (2006.01)
*H01R 4/18* (2006.01)

(52) U.S. Cl.
CPC ............... *A61N 1/05* (2013.01); *H01R 4/183* (2013.01)

(58) Field of Classification Search
CPC ...... A61N 1/05; A61N 1/056; A61N 1/37516; H01R 2201/12; H01R 43/02; H01R 43/05; H01R 43/28; H01R 4/026
See application file for complete search history.

(56) References Cited

U.S. PATENT DOCUMENTS

| | | | |
|---|---|---|---|
| 9,560,979 B2 * | 2/2017 | Shan | ............ A61N 1/0529 |
| 2003/0036788 A1 | 2/2003 | Coe et al. | |
| 2008/0178449 A1 | 7/2008 | Huotari et al. | |
| 2012/0071958 A1 | 3/2012 | Klardie et al. | |
| 2013/0098680 A1 | 4/2013 | Nabeta et al. | |
| 2014/0107455 A1 | 4/2014 | Regnier et al. | |
| 2015/0157851 A1 | 6/2015 | Sefkow et al. | |
| 2020/0009370 A1 * | 1/2020 | Julien | ............ A61N 1/37516 |

FOREIGN PATENT DOCUMENTS

| | | |
|---|---|---|
| DE | 19 25 238 U | 10/1965 |
| EP | 2 674 190 B1 | 12/2013 |
| EP | 2 719 422 B1 | 4/2014 |
| JP | 2013-085885 A | 5/2013 |
| WO | WO-2012/039919 A2 | 3/2012 |

OTHER PUBLICATIONS

Office Action on Japanese patent application No. 2019-125662 dated Jun. 18, 2020.
Office Action issued in EP Application No. 19184141.0 dated Apr. 13, 2021.
Search Report on French Patent Application No. 1856248 dated Mar. 18, 2019. 7 pages.
Official Action for European Application No. EP19184141.0 dated Nov. 14, 2019, 9 pages.

* cited by examiner

*Primary Examiner* — Minh N Trinh
(74) *Attorney, Agent, or Firm* — Foley & Lardner LLP

(57) ABSTRACT

The present invention relates to a method for connecting a strand of a multi-strand cable to an electrode of an implantable medical device. The method includes cutting a strand of the multi-strand cable lifting at least one of the free ends, stripping the end of the lifted strand, placing an electrode around the multi-strand cable to partially cover the end of the lifted and stripped stand, and connecting at least one portion of the stripped end of the strand to the electrode.

10 Claims, 4 Drawing Sheets

CONNECTION METHOD FOR CONNECTING AN ISOLATED MICRO-CONDUCTOR

CROSS-REFERENCE TO RELATED PATENT APPLICATIONS

This application claims the benefit of and priority to French Patent Application No. 1856248, filed Jul. 6, 2018, which is incorporated herein by reference in its entirety.

BACKGROUND

The present invention relates to a method for connecting an isolated micro-conductor of a multi-micro-conductor cable, in particular to an electrode of an implantable medical device.

In particular, the present invention relates to the connection of an isolated microcable, also called strand, of a multi-stranded microcable to a stimulation electrode, such that each individual strand is electrically insulated from the other strands by an insulating sheath, in particular by a polymer sheath.

A composite assembly of such a microcable is intrinsically difficult to connect to an electrode, for example in the context of the manufacture of an implant, due to the size of the conductive strands (of the order of 100 µm), that is to say, strands, to connect at the electrode, but also related to the very thin thickness of the insulators—to guarantee the small size of the assembly, and finally, to the difficulties related to the proximity of the conductors to each other and to the reliability over time of the contact, in an in vivo medium.

EP 2 719 422 B1 describes an approach for locally performing an ablation of the insulation, and deposit a conductive glue. However, the conductive adhesive, used in a biological environment, is likely to be biodegraded, which can affect the electrical contact. Another difficulty comes from the step of depositing in a cavity of 50 µm-80 µm a reproducible amount of conductive adhesive.

EP 2 674 190 B1 describes an additional manufacturing, by successive addition of layers of metallic material, making it possible to contact the micro-cable with an electrode incorporating a contactor mechanism. This type of mechanism, however, has disadvantages in terms of accuracy of the contact and of its stability, because it depends on the tolerance of the mechanical parts in contact, as well as of the insulation thickness. Furthermore, this technique does not seem suitable for a multi-strand cable.

SUMMARY

The object of the invention is therefore to provide a connection method that can improve a low resistance electrical contact, robust and durable over time in a structure of the order of one micron (1 µm) —especially in a biological medium, with mechanical stress between an insulated micro-conductor (strand) and an electrode.

The object of the present invention is achieved by a method for connecting a strand of a multi-strand cable to a conductive element, in particular to an electrode, comprising the steps of:

a) cutting a strand of the multi-strand cable to form two free ends at the cut of the strand;

b) lifting at least one of the free ends relative to the rest of the multi-strand cable;

c) at least partially stripping the end of the lifted strand;

d) placing a conductive element around the multi-strand cable so as to partially cover the lifted and stripped strand end;

e) connecting at least a portion of the stripped end of the strand to the conductive element.

The extraction of one of the strands of the microcable makes it possible to extract the entire insulating coating in the weld zone and thus avoid difficulties related to the presence of polymer in a weld, in particular a laser weld, which affects its quality, especially on a micron scale.

This method, in addition of allowing reliable welding conditions, also improves the long-term robustness of the electrical junction between the strand isolated from the rest of the microcable and of the electrode.

The present invention may be further improved by the following embodiments.

According to another embodiment of the invention, step b) may comprise: covering the other of the free ends of the strand by introducing an insulating sleeve around the cable. This insulating sleeve makes it possible to prevent the other end from escaping or lifting on the rest of the cable.

According to another embodiment of the invention, step b) may also comprise laying a second sleeve and/or a polymer adhesive around the multi-strand cable in order to control the length (L) of the lifted strand end from the rest of the multi-strand cable. This second sleeve also allows, depending on its position, to secure the length of the end of the strand that has been lifted and maintain this length through the second sleeve.

According to another embodiment of the invention, step a) and c) may comprise laser cutting and/or laser ablation or the use of a cutting mechanical device. Thus, this process can be carried out using controlled technologies. In addition, according to the method of the present invention, the weld can be performed with visual control which further improves the reliability of the weld.

The object of the present invention is also achieved by a method for connecting a strand of a multi-strand cable to a conductive element, in particular to an electrode, comprising the 5 steps of:

a) cutting a strand of the multi-strand cable to form two free ends at the cut of the strand;

b) lifting at least one of the free ends relative to the rest of the multi-strand cable;

c) placing a metal hypotube around the end of the lifted strand so that the hypotube is electrically connected to the end of the strand;

d) placing a conductive element around the multi-strand cable so as to partially cover the metal hypotube;

e) connecting at least a portion of the metal hypotube to the conductive element.

This method, through the use of metal hypotube, offers reliable welding conditions, and also improves the long-term robustness of the electrical junction between the strand isolated from the rest of the microcable and of the electrode. Indeed, the welding is performed at the hypotube which avoids difficulties related to the presence of polymer in a weld, especially in a laser weld.

The two methods of the present invention described above may be further improved by the following embodiments.

According to another embodiment of the invention, the connection at step e) can be performed by laser welding, crimping or electrical welding.

According to another embodiment of the invention, each method may comprise a step f) of laying a polymer sheath in order to coat the multi-strand cable and the electrode welded to the cable. This step advantageously adds an insulating barrier to the microcable to which the electrode is welded.

According to another embodiment of the invention, the conductive element may be an electrode. Advantageously, the electrode may be in the form of a ring such that the ring may comprise a central hole or a slot configured to perform the welding in step e).

In another embodiment of the invention, the electrode may be in the form of a ring such that the ring may comprise an internal cavity adapted to the size of the end of the lifted strand. This internal cavity makes it possible to leave the necessary space at the end of the strand to weld and thus further improves the electrical contact area.

In another embodiment of the invention, the diameter of a strand—taking into consideration the conductive portion and the insulating portion of the strand—may be between 10 microns and 200 microns; the diameter of the multi-stranded microcable, that is to say the diameter of the entire cable, can be less than 2 French (or 0.66 mm) and can be made from biocompatible materials.

For the insulating part of the strand, materials such as fluoropolymers, in particular PTFE (polytetrafluoroethylene), FEP (perfluorinated propylene), PFA (perfluoroalkoxy copolymer resin), THV (tetrafluoroethylene, hexafluoropropylene, vinylidene fluoride), PVDF (polyvinylidene fluoride), EFEP (ethylene propylene fluorinated ethylene), or ETFE (ethylene tetrafluoroethylene). In addition, polyurethanes (PU), polyesters (PET), polyamides (PA), polycarbonates (PC), polyimides, fluorinated polymers, polyether ether ketone (PEEK), poly-p-xylylene (parylene), or polymethyl methacrylate (PMM) can also be used, as mentioned in EP3058983.

The conductive part of the core of the strands can be made of materials such as stainless steels, cobalt alloys, titanium, NiTi alloy (nitinol), tantalum (Ta), tungsten (W), iridium (Ir), platinum (Pt), gold (Au) and their alloys as mentioned in EP2581107. Thus, the microcable is adapted to be used in combination with implantable devices.

The present invention is also achieved by a multi-strand microcable comprising at least one conductive element such that at least one end of a strand of the microcable is partially stripped so that the partially stripped portion of the strand is connected, in particular by welding, crimping or electric welding, to the conductor element.

Thus, the contact surface between the insulated strand and the conductive element is improved.

In another embodiment of the invention, the microcable can comprise an insulating sleeve positioned around the cable and on which the end of the strand is positioned. This insulating sleeve makes it possible to prevent the other end from escaping or lifting on the rest of the cable.

Alternatively, the present invention is also achieved by a multi-strand microcable comprising at least one conductive element and a metal hypotube such that at least one end of a strand of the microcable is at least partially in electrical contact with the hypotube, so that the hypotube is connected, in particular by welding, crimping or electrical welding, to the conductive element.

The present invention, relating to a multi-stranded microcable, can be further improved thanks to the following embodiments.

According to another embodiment of the invention, the conductive element may be a ring-shaped electrode such that the ring comprises a central hole or a slot configured to make the weld with the portion of one end of the strand.

According to another embodiment of the invention, the conductive element may be a ring-shaped electrode such that the ring comprises an internal cavity adapted to the size of the end of the strand arranged partially above the insulating sleeve. This internal cavity makes it possible to leave the necessary space at the end of the strand to be welded and thus improves more the electrical contact surface.

According to another embodiment of the invention, the diameter of a strand—taking into consideration the conductive portion and the insulating portion of the strand—may be between 10 and 200 µm; the diameter of the multi-stranded microcable, that is to say the diameter of the entire cable, can be less than 2 French (or 0.66 mm) and can be made from biocompatible materials. For the insulating part of the strand, materials such as fluoropolymers, in particular PTFE (polytetrafluoroethylene), FEP (perfluorinated propylene), PFA (perfluoroalkoxy copolymer resin), THV (tetrafluoroethylene, hexafluoropropylene, vinylidene fluoride), PVDF (polyvinylidene fluoride), EFEP (ethylene propylene fluorinated ethylene), or ETFE (ethylene tetrafluoroethylene). In addition, polyurethanes (PU), polyesters (PET), polyamides (PA), polycarbonates (PC), polyimides, fluorinated polymers, polyether ether ketone (PEEK), poly-p-xylylene (parylene), or polymethyl methacrylate (PMM) can also be used, as mentioned in EP3058983.

The conductive part of the core of the strands can be made of materials such as stainless steels, cobalt alloys, titanium, NiTi alloy (nitinol), tantalum (Ta), tungsten (W), iridium (Ir), platinum (Pt), gold (Au) and their alloys as mentioned in EP2581107. Thus, the microcable is adapted to be used in combination with implantable devices.

The present invention, relating to the method or to the multi-strand microcable, can be further improved according to the following variants.

According to a variant of the invention, the welding can be performed at the two free ends of the same strand to ensure redundancy of the connection.

In yet another variant, two opposing strands can be cut, lifted and partially extracted from the rest of the cable and welded on both sides.

Finally, in another variant, the separation of the strands of the same cable into a number n of sub-cables or wires makes it possible to make redundancy of welds and thus to improve the reliability of the electrical contact with the conductive element by increase in the number of welds. Especially in the case wherein one of the welds breaks, the remaining n−1 welds make it possible to ensure the electrical contact. Thus, the weld redundancy improves the robustness of the electrical contact.

BRIEF DESCRIPTION OF THE DRAWINGS

The invention and its advantages will be explained in more detail in the following by means of preferred embodiments and relying in particular on the accompanying figures, wherein.

DETAILED DESCRIPTION

Those skilled in the art will appreciate that the present invention can be applied essentially to any type of connector, particularly to any type of micro-connector configured for implantable devices.

Figure 1:
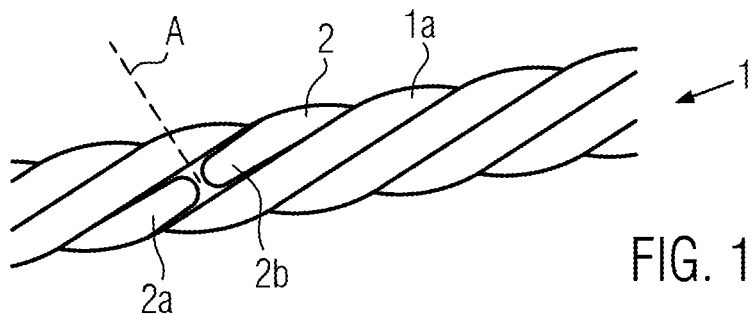
FIG. 1 schematically illustrates a microcable in step a) of the method according to the present invention.

FIG. 1 illustrates a multi-strand microcable 1 whose dimensions are of the order of one micron and which is made from biocompatible materials. The microcable 1 is formed of several strands, each strand being provided with a sheath 1a of insulating polymer. In the process step shown in FIG. 1, one of the strands was laser cut, indicated by the arrow A, so that the strand 2 is provided with two free ends 2a and 2b.

In a variant, the same strand is cut in several places.

In another embodiment, the cutting of the strand 2 is carried out by means of a mechanical device such as micro-knife, pliers, etc.

Figure 2:
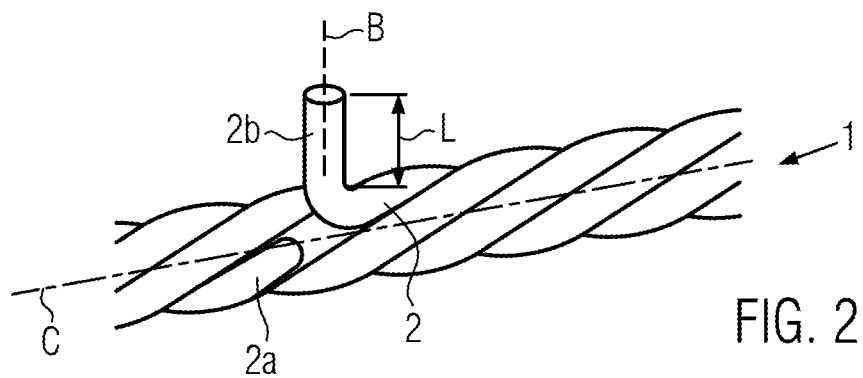
FIGS. 2 and 3 schematically illustrate a microcable in step b) of the method according to the present invention.

In the step illustrated in FIG. 2, a portion of length L of the free end 2b of the strand 2 has been lifted and partially extracted from the rest of the microcable 1 so that the axis B of the end 2b of the strand 2 is substantially perpendicular to the axis C of rotation of the cable 1.

The end 2a is not lifted relative to the rest of the microcable 1.

Figure 3:
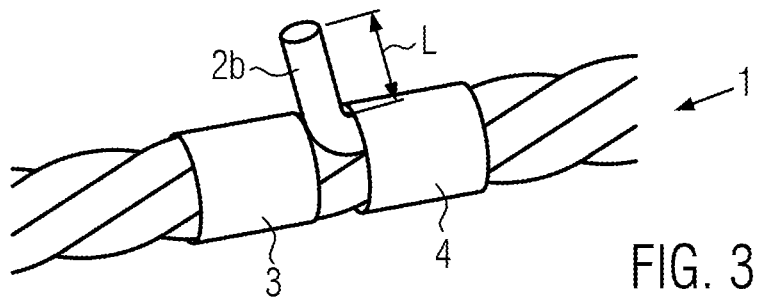

In the step illustrated in FIG. 3, a first insulating sleeve 3, made of polymer material, is inserted, like a ring, around the cable 1 so as to cover the end 2a (which thus becomes not visible on the FIG. 3).

A second sleeve 4, also insulating and of polymeric material, is threaded around the cable 1 so as to cover the portion of the end 2b that has not been extracted in the previous step illustrated by FIG. 2. Thus, this second sleeve 4 ensures that only the length portion L of the end 2b protrudes on the cable 1.

In another embodiment, a polymer adhesive may be used to hold the portion of the end 2b that is not intended to be lifted and partially extracted from the cable 1.

In the embodiment illustrated in FIG. 3, the cable 1 is thus provided with two sleeves 3 and 4 such that the portion of length L of the end 2b projects between the two sleeves 3 and 4.

Figure 4:
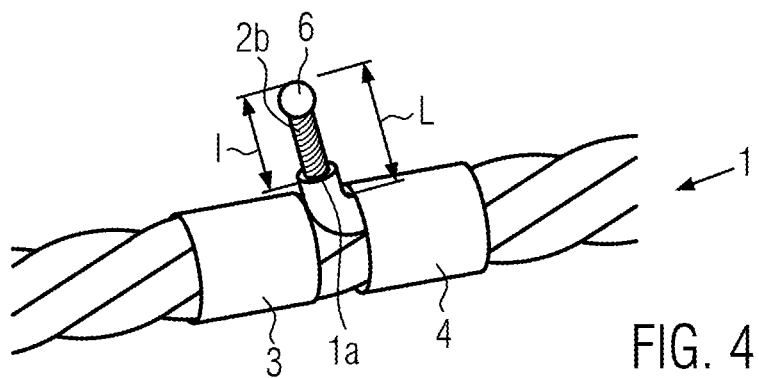
FIGS. 4 and 5 schematically illustrate a microcable in steps c) and d) of the method according to the present invention.

FIG. 4 illustrates a step wherein a portion 1 of the length portion L of the end 2b is stripped of its polymer insulation 1a by laser ablation. Therefore, the part I of the end 2b corresponds to the conductive portion of the strand 2. A spherical tip 6 is formed at the outermost point of the end 2b. This spherical tip 6, also called "ball tip", allows to merge, in a kind of ball, the multiple metal strands constituting the strand 2, which prevents individual strands from escaping and thus reduce the reliability of the electrical contact. The spherical tip 6 also provides a larger contact area, further improving the electrical reliability of the contact.

In another embodiment, the insulation of the length L of the end 2b is removed mechanically.

Alternatives to the removal of a portion 1 of the insulating portion 1a and to the formation of a spherical tip 6 at the end of the end 2b are described in FIG. 11.

Figure 5:
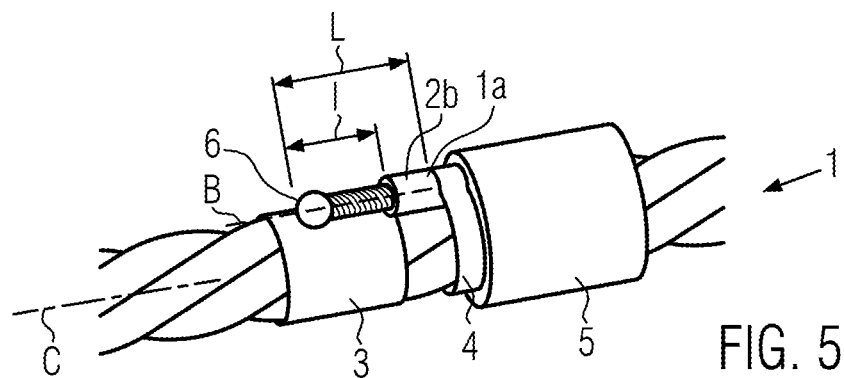

In FIG. 5, a cylindrical electrode 5 is threaded around the microcable 1 so as to partially cover the sleeve 4 on the opposite side to that of the sleeve 3. The end 2b is arranged so as to be placed on the sleeve 3 such that the axis B of the portion of length L of strand 2 is parallel to the axis C of the cable 1.

Figure 6:
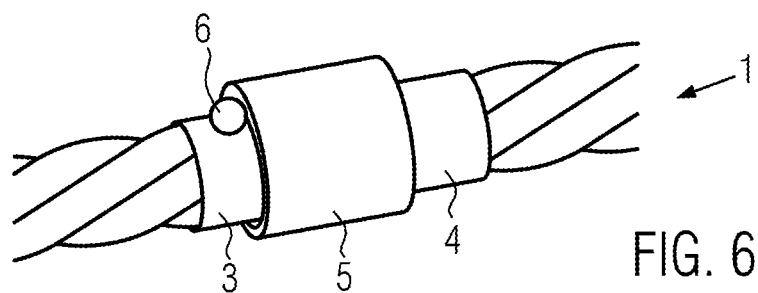
FIG. 6 schematically illustrates a microcable in step e) of the method according to the present invention.

In the step illustrated in FIG. 6, the cylindrical electrode 5 is moved to the sleeve 3 so as to cover almost completely the end 2b. Thus, only the spherical tip 6 of the end 2b is not covered by the electrode 5. It is the spherical tip 6 of the strand 2, which corresponds to a conductive part of the strand 2 because it is devoid of polymer insulation 1a, which is then welded to the laser electrode 5. Advantageously, such a weld can be performed with a visual control.

In addition, the method of the present invention makes it possible to avoid the difficulties associated with the presence of polymer in a laser welding, which affects its quality, in particular on a scale of about one micron.

In another embodiment, the cylindrical electrode 5 is crimped in the position shown in FIG. 6 before the welding step, in order to mechanically maintain its position.

Figure 7:
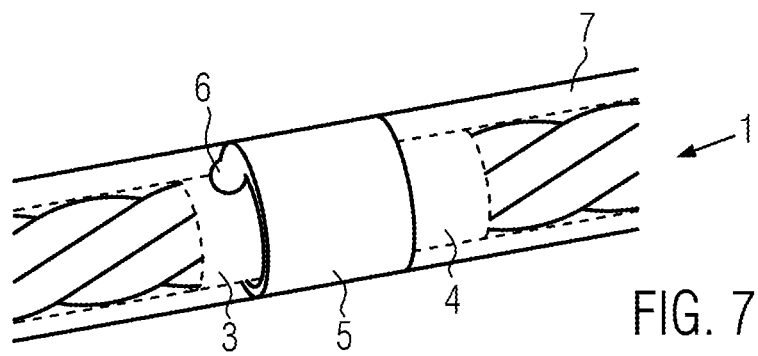
FIG. 7 schematically illustrates a microcable in step f) of the method according to the present invention.

In FIG. 7, a polymer sheath 7 is made in order to coat the multi-strand cable 1 and the electrode 5 welded to the cable 1. This sheath can for example be produced by the "reflow" technique, which allows melting the polymer to fill the remaining holes and spaces. This technique makes it possible to obtain an isodiametric finished product and to add an insulating barrier to the assembly.

FIGS. 8a, 8b, 9 and 10 illustrate variants of the electrode 5.

Figure 8A:
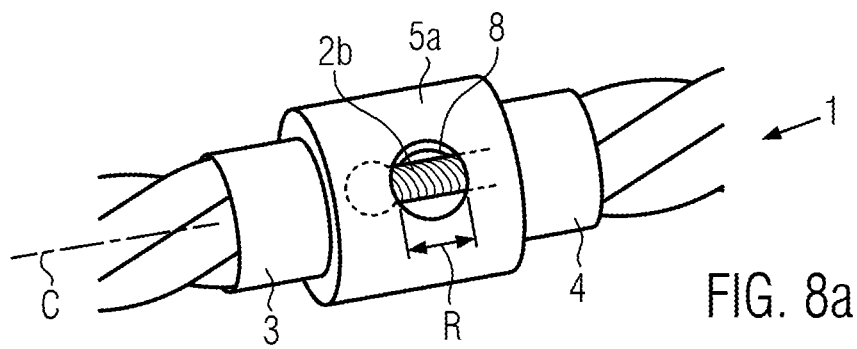
FIGS. 8a, 8b, 9 and 10 schematically illustrate alternative embodiments of a conductive element.
Figure 8B:
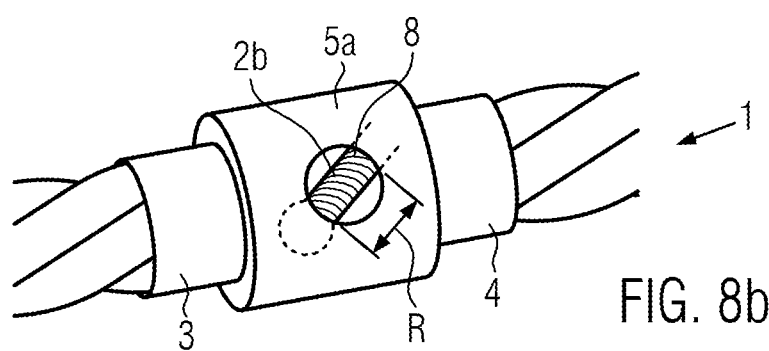

In the variant illustrated in FIGS. 8a and 8b, the electrode 5a is a ring with a central hole 8. In FIG. 8a, the strand 2b isolated from the rest of the cable 1 is aligned with the axis C of the cable 1. In FIG. 8b, the strand 2b is in rotation with respect to the cable 1. However, in both variants, the welding is made at the central hole 8 which is arranged above a portion R of strand 2b.

Figure 9:
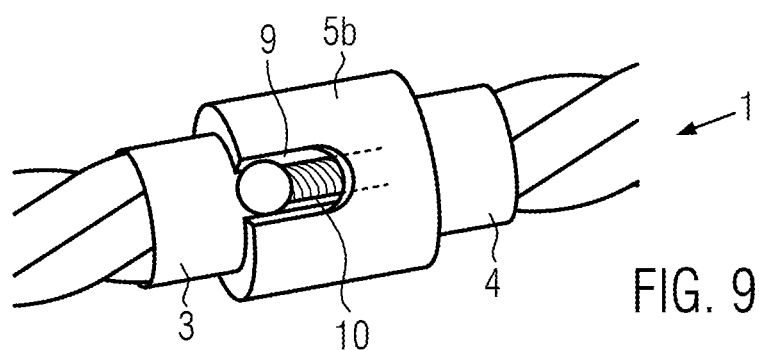

In FIG. 9, the electrode 5b is a ring with a "U" shape slot 9, also called ring "with frontal loading". In another embodiment, the slot could be in a "V" shape, an arc shape, etc. In this embodiment, the end of the strand 2b is arranged to be aligned between the longitudinal sides 9 and 10 of the slot 9. The weld is thus made at the slot 9 between the strand 2b and the ring 5b.

Figure 10:
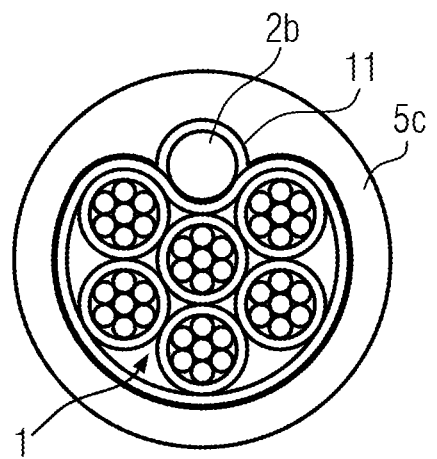

In the embodiment of FIG. 10, the electrode 5c is a ring comprising an internal cavity 11. The internal cavity 11 of the ring 5c is adapted to the diameter of the end of the lifted strand 2b. The end of the strand 2b is thus partially housed in the internal cavity 11. This internal cavity 11 makes it possible to leave the space required for the end of the strand 2b to be welded and thus makes it possible to improve the electrical contact surface.

FIG. 11 illustrates alternatives to the formation of a spherical tip 6 for making electrical contact with the conductive member 5, as described above and shown in FIG. 11a.

Figure 11A:
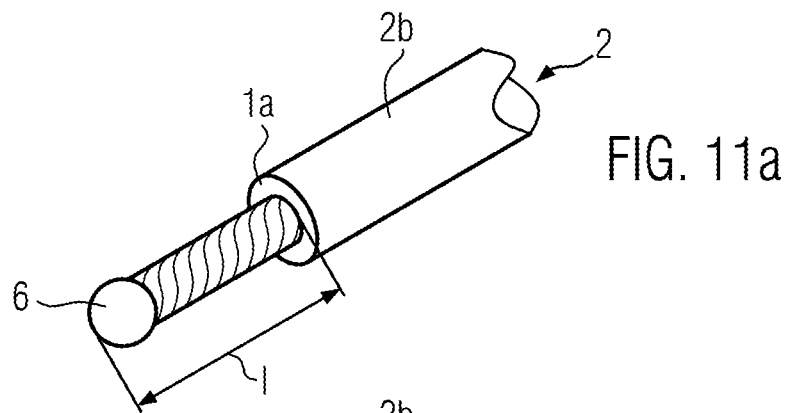
FIGS. 11a-d schematically illustrate alternative embodiments of the strand to connect.
Figure 11B:
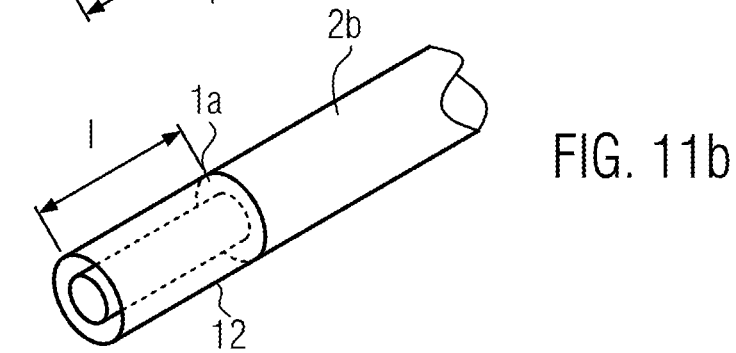

Thus, in the variant illustrated in FIG. 11b, the end 2b of the strand 2 has been stripped over a length l, and then a hollow metal hypotube 12 has been inserted around the length l stripped of the strand 2. The contact surface between the stripped part 1 and the metallic hypotube 12 ensures electrical contact.

Figure 11C:
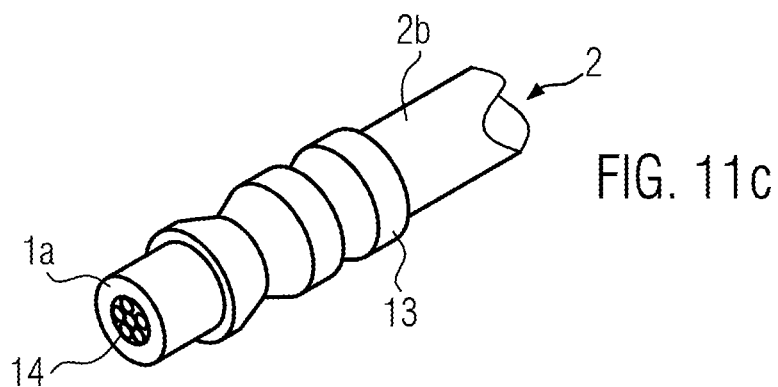

In the variant illustrated in FIG. 11c, the end 2b of the strand 2 is not stripped and therefore still comprises its insulating sheath 1a. A hollow metal hypotube 13 has been inserted around the end 2b and crimped so that the crimping of hypotube 13 is perforating to make an electrical contact with the conductive portion 14 of the strand 2.

Figure 11D:
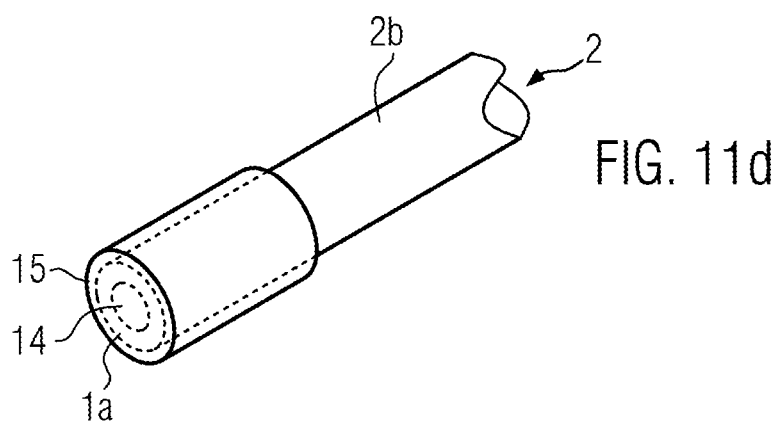

The variant of FIG. 11d shows a strand 2 whose end 2b is not stripped and therefore still comprises its insulating sheath 1a. A hollow metal hypotube 13 has been inserted around the end 2b and welded to the end 2b, in particular welded to the conductive portion 14 of the strand 2.

In yet another variant which is not illustrated, the welding can be performed at the two free ends 2a, 2b of the same strand 2 to ensure redundancy of the connection.

In yet another variant which is not illustrated, two opposing strands can be cut, lifted and partially removed from the rest of the cable and welded on both sides.

Finally, in another variant not shown, the separation of the strands of the same cable in a number n sub-cables or wires makes it possible to make the redundancy of welding and thus to improve the reliability of the electrical contact with the conductor element by increasing the number of welds. Especially in the case wherein one of the welds breaks, the n−1 welds make it possible to ensure the electrical contact. Thus, the weld redundancy improves the robustness of the electrical contact.

The embodiments and alternatives discussed above may be combined to form more advantageous alternative embodiments of the present invention.

What is claimed is:

1. A method for connecting a strand of a multi-strand cable to an electrode of an implantable medical device, comprising the steps of:
   cutting the strand of the multi-strand cable to form two free ends at the cut of the strand;
   lifting at least one of the free ends relative to the rest of the multi-strand cable;
   at least partially stripping the end of the lifted strand;
   placing the electrode around the multi-strand cable so as to partially cover the end of the lifted and stripped strand;
   connecting at least one portion of the stripped end of the strand to the electrode.

2. The method according to claim 1, the method further comprising:
   covering the other of the free ends of the strand by introducing an insulating sleeve-around the multi-strand cable.

3. The method according to claim 2, the method further comprising:
   laying at least one of a second sleeve or a polymer glue around the multi-strand cable to control the length of the end of the lifted strand relative to the rest of the multi-strand cable.

4. The method according to claim 1, wherein the cutting comprises at least one of a laser cut, a laser ablation, or the use of a mechanical cutting device.

5. A method for connecting a strand of a multi-strand cable to an electrode of an implantable medical device, comprising the steps of:
   cutting the strand of the multi-strand cable to form two free ends at the cut of the strand;
   lifting at least one of the free ends relative to the rest of the multi-strand cable;
   placing a metal hypotube around the end of the lifted strand so that the metal hypotube is electrically connected to the end of the strand;
   placing the electrode around the multi-strand cable so as to partially cover the metal hypotube;
   connecting at least a portion of the metal hypotube to the electrode.

6. The method according to claim 5, wherein the connection is performed by laser welding, crimping or electric welding.

7. The method according to claim 5, further comprising:
   laying a polymer sheath in order to coat the multi-strand cable and the electrode welded to the multi-strand cable.

8. The method according to claim 5, wherein the electrode is a ring-shaped electrode such that the ring comprises a central hole or a slot configured to perform the welding in step.

9. The method according to claim 5, wherein the electrode is a ring-shaped electrode such that the ring comprises an internal cavity adapted to the dimension of the end of the lifted strand.

10. The method according claim 5, such that the diameter of the strand is between 10 µm and 200 µm, and the diameter of the multi-strand microcable, that is to say the diameter of the entire multi-strand microcable, is less than 0.66 mm and is made from biocompatible materials.

* * * * *